United States Patent
Fanelli et al.

(10) Patent No.: US 9,867,615 B2
(45) Date of Patent: Jan. 16, 2018

(54) SURGICAL INSTRUMENT WITH ARTICULATION LOCK HAVING A DETENTING BINARY SPRING

(71) Applicant: Ethicon Endo-Surgery, Inc., Cincinnati, OH (US)

(72) Inventors: Nicholas Fanelli, Morrow, OH (US); Jeffrey C. Gagel, Loveland, OH (US); Jason E. Zerkle, Blanchester, OH (US); Robert J. Simms, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 1017 days.

(21) Appl. No.: 13/780,162

(22) Filed: Feb. 28, 2013

(65) Prior Publication Data

US 2014/0239040 A1 Aug. 28, 2014

(51) Int. Cl.
 *A61B 17/068* (2006.01)
 *A61B 17/072* (2006.01)
 *A61B 17/29* (2006.01)
 *A61B 17/00* (2006.01)

(52) U.S. Cl.
 CPC ............ *A61B 17/07207* (2013.01); *A61B 2017/00398* (2013.01); *A61B 2017/2927* (2013.01); *A61B 2017/2929* (2013.01); *A61B 2017/2939* (2013.01); *A61B 2017/2943* (2013.01); *A61B 2017/2946* (2013.01)

(58) Field of Classification Search
 CPC .. A61B 17/068; A61B 17/00; A61B 17/07207
 USPC ...................... 227/175.1–180.2, 19
 See application file for complete search history.

(56) References Cited

U.S. PATENT DOCUMENTS

| 4,805,823 | A | 2/1989 | Rothfuss |
| 5,307,976 | A | 5/1994 | Olson et al. |
| 5,415,334 | A | 5/1995 | Williamson, IV et al. |
| 5,465,895 | A | 11/1995 | Knodel et al. |
| 5,597,107 | A | 1/1997 | Knodel et al. |

(Continued)

FOREIGN PATENT DOCUMENTS

| EP | 1 621 146 A2 | 2/2006 |
| EP | 1 749 485 A1 | 2/2007 |

(Continued)

OTHER PUBLICATIONS

U.S. Appl. No. 13/780,067, filed Feb. 28, 2013.

(Continued)

*Primary Examiner* — Stephen F Gerrity
*Assistant Examiner* — Mary Hibbert
(74) *Attorney, Agent, or Firm* — Frost Brown Todd LLC

(57) ABSTRACT

A apparatus includes a shaft, an end effector, an articulation joint, and a locking feature. The end effector is pivotable from a first position to a second position. The end effector is aligned with a longitudinal axis of the shaft in the first position and angled relative to the longitudinal axis of the shaft in the second position. The articulation joint couples the shaft with the end effector and pivots the end effector from the first position to the second position. The locking feature is coupled with the articulation joint and translates from a proximal position to a distal position. The locking feature locks the articulation joint when the locking feature is in the distal position.

19 Claims, 22 Drawing Sheets

(56) References Cited

U.S. PATENT DOCUMENTS

| | | |
|---|---|---|
| 5,632,432 A | 5/1997 | Schulze et al. |
| 5,662,667 A | 9/1997 | Knodel |
| 5,673,840 A | 10/1997 | Schulze et al. |
| 5,673,841 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,500,176 B1 | 12/2002 | Truckai et al. |
| 6,783,524 B2 | 8/2004 | Anderson et al. |
| 6,978,921 B2 | 12/2005 | Shelton, IV et al. |
| 7,000,818 B2 | 2/2006 | Shelton, IV et al. |
| 7,044,352 B2 | 5/2006 | Shelton, IV et al. |
| 7,143,923 B2 | 12/2006 | Shelton, IV et al. |
| 7,303,108 B2 | 12/2007 | Shelton, IV et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,419,080 B2 | 9/2008 | Smith et al. |
| 7,434,715 B2 | 10/2008 | Shelton, IV et al. |
| 7,455,208 B2 | 11/2008 | Wales et al. |
| 7,481,824 B2 | 1/2009 | Gillum et al. |
| 7,490,749 B2 | 2/2009 | Schall et al. |
| 7,524,320 B2 | 4/2009 | Tierney et al. |
| 7,549,564 B2 | 6/2009 | Boudreaux |
| 7,644,848 B2 | 1/2010 | Swayze et al. |
| 7,658,311 B2 | 2/2010 | Boudreaux |
| 7,690,547 B2 | 4/2010 | Racenet et al. |
| 7,691,098 B2 | 4/2010 | Wallace et al. |
| 7,721,930 B2 | 5/2010 | McKenna et al. |
| 7,753,245 B2 | 7/2010 | Boudreaux et al. |
| 7,798,386 B2 | 9/2010 | Schall et al. |
| 7,806,891 B2 | 10/2010 | Nowlin et al. |
| 7,954,684 B2 | 6/2011 | Boudreaux |
| 8,210,411 B2 | 7/2012 | Yates et al. |
| 8,245,898 B2 | 8/2012 | Smith et al. |
| 8,408,439 B2 | 4/2013 | Huang et al. |
| 8,453,914 B2 | 6/2013 | Laurent et al. |
| 8,461,744 B2 | 6/2013 | Wiener et al. |
| 8,479,969 B2 | 7/2013 | Shelton, IV et al. |
| 8,573,461 B2 | 11/2013 | Shelton, IV et al. |
| 8,573,465 B2 | 11/2013 | Shelton, IV |
| 8,579,176 B2 | 11/2013 | Smith et al. |
| 8,602,288 B2 | 12/2013 | Shelton, IV et al. |
| 8,616,431 B2 | 12/2013 | Timm et al. |
| 2006/0025809 A1* | 2/2006 | Shelton, IV ..... A61B 17/07207 606/205 |
| 2007/0073341 A1 | 3/2007 | Smith et al. |
| 2010/0193566 A1* | 8/2010 | Scheib ............ A61B 17/07207 227/175.2 |
| 2012/0138660 A1 | 6/2012 | Shelton, IV |
| 2012/0199630 A1 | 8/2012 | Shelton, IV |
| 2012/0199632 A1 | 8/2012 | Spivey et al. |
| 2012/0203247 A1 | 8/2012 | Shelton, IV et al. |
| 2013/0012957 A1 | 1/2013 | Shelton, IV et al. |

FOREIGN PATENT DOCUMENTS

| | | |
|---|---|---|
| EP | 2 042 107 A1 | 4/2009 |
| WO | WO 98/14124 A1 | 4/1998 |

OTHER PUBLICATIONS

U.S. Appl. No. 13/780,082, filed Feb. 28, 2013.
U.S. Appl. No. 13/780,106, filed Feb. 28, 2013.
U.S. Appl. No. 13/780,120, filed Feb. 28, 2013.
U.S. Appl. No. 13/780,379, filed Feb. 28, 2013.
U.S. Appl. No. 13/780,402, filed Feb. 28, 2013.
U.S. Appl. No. 13/780,417, filed Feb. 28, 2013.
European Search Report and Written Opinion dated Jun. 20, 2014 for Application No. EP 14157361.8, 7 pgs.
International Search Report and Written Opinion dated Apr. 28, 2014 for Application No. PCT/US2014/016211, 11 pgs.
Chinese Office Action, Notification of the First Office Action, dated Mar. 21, 2017 for Application No. 201480011017.5, 8 pgs.
European Search Report, Extended, and Written Opinion dated May 15, 2017 for Application No. EP 16203642.0, 9 pgs.

* cited by examiner

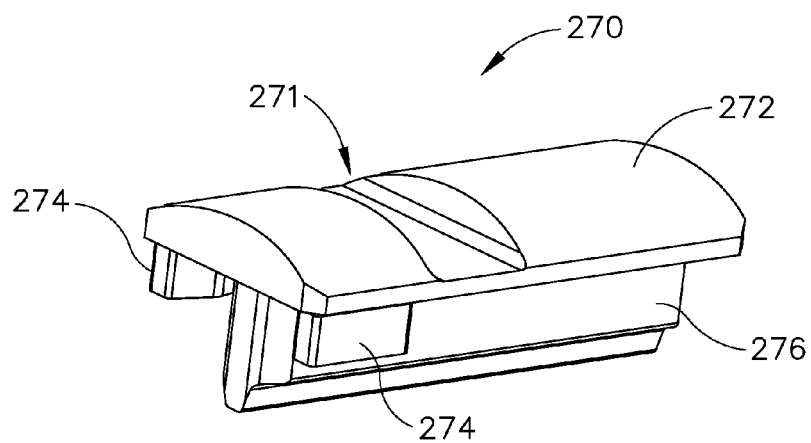
Fig.18
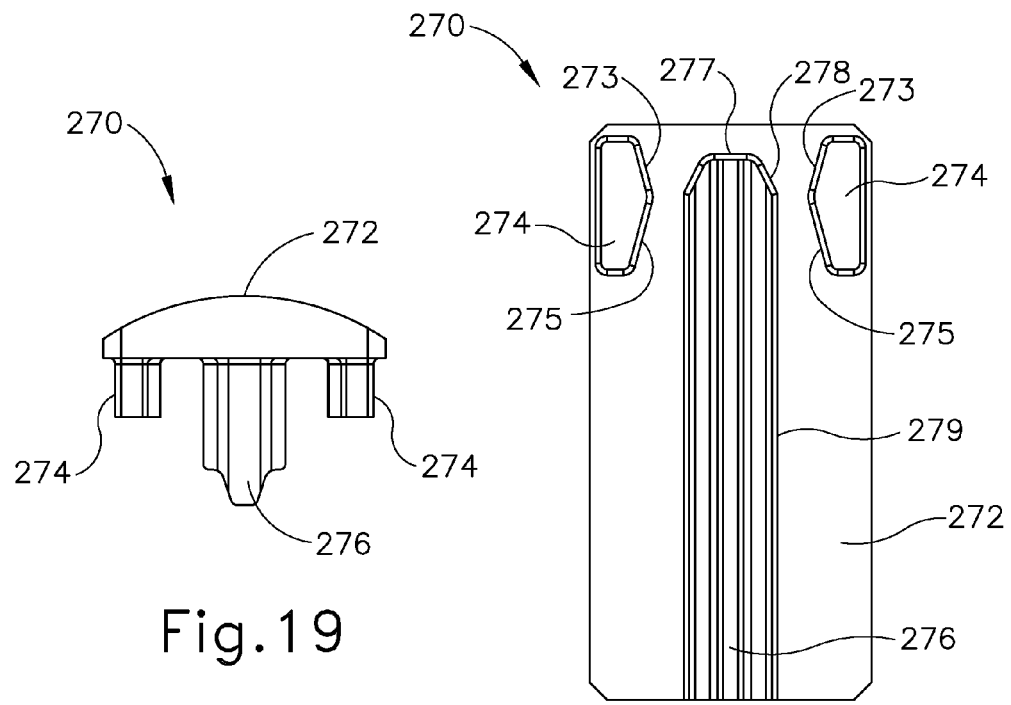
Fig.19
Fig.20

SURGICAL INSTRUMENT WITH ARTICULATION LOCK HAVING A DETENTING BINARY SPRING

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, issued Apr. 2, 2013 as U.S. Pat. No. 8,408,439; and U.S. Pub. No. 2012/0239012, entitled "Motor-Driven Surgical Cutting Instrument with Electric Actuator Directional Control Assembly," published Sep. 20, 2012, issued Jun. 4, 2013 as U.S. Pat. No. 8,453,914. The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 18 depicts a perspective view of an exemplary locking sled of the articulation joint of FIG. 12;

FIG. 19 depicts a front view of the locking sled of FIG. 18;

FIG. 20 depicts a bottom view of the locking sled of FIG. 18;

Figure 1:
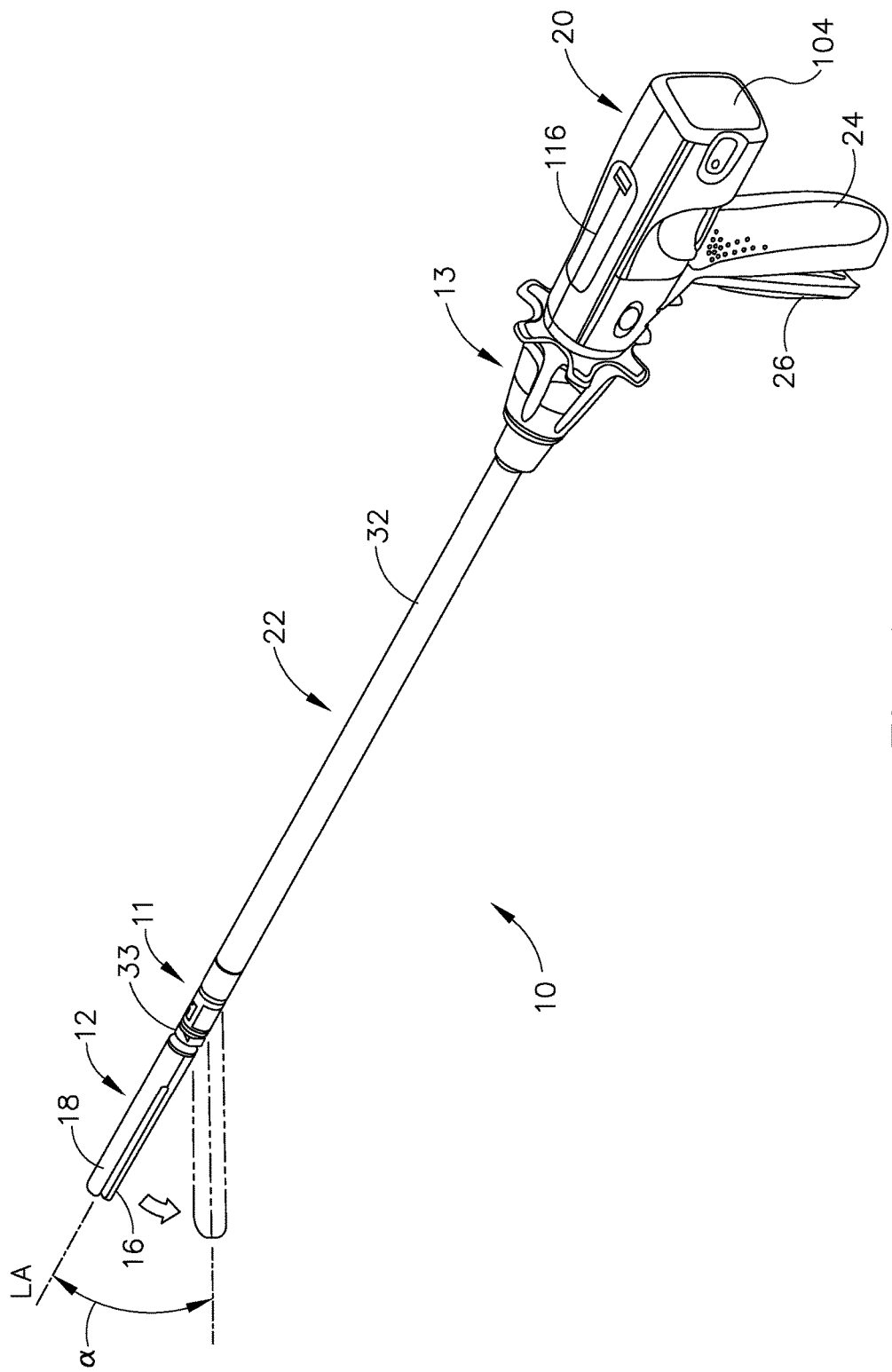
FIG. 1 depicts a perspective view of an exemplary articulating surgical stapling instrument.
Figure 2:
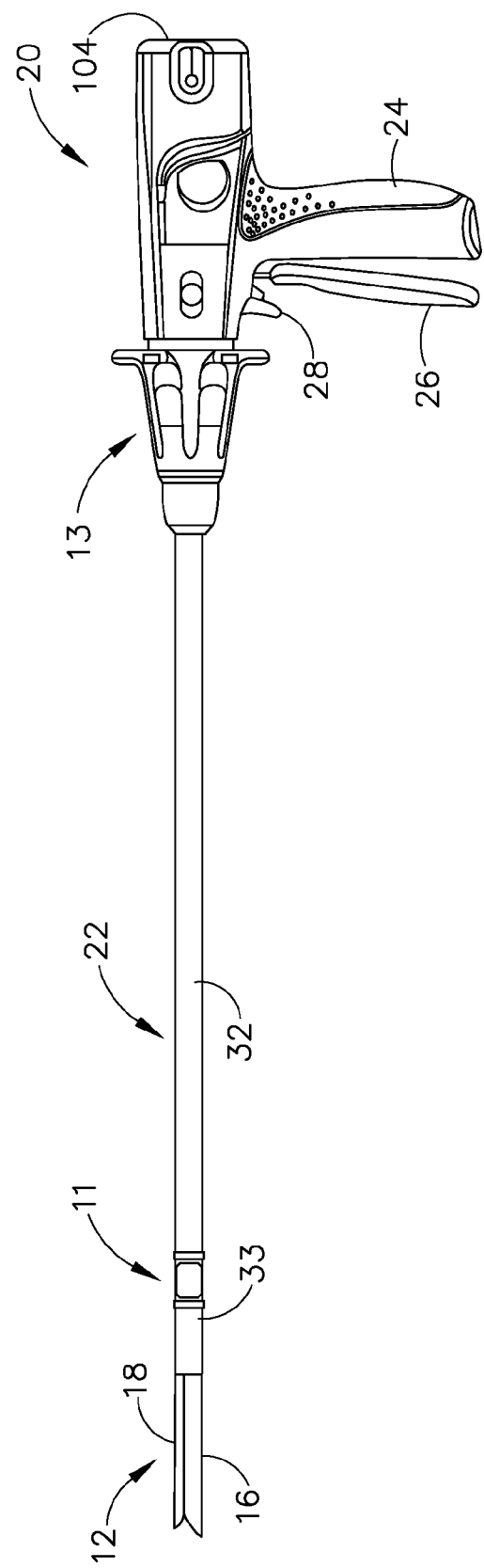
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. patent application Ser. No. 13/780,402, entitled "Surgical Instrument with Multi-Diameter Shaft," filed Feb. 28, 2013, now U.S. Pat. No. 9,795,379, issued Oct. 24, 2017, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. patent application Ser. No. 13/780,067, entitled "Surgical Instrument End Effector Articulation Drive with Pinion and Opposing Racks," filed Feb. 28, 2013, now U.S. Pat. No. 9,186,067, issued Nov. 17, 2015, the disclosure of which is incorporated by reference herein. Articulation joint (11) may also be constructed and operable in accordance with at least some of the teachings of U.S. patent application Ser. No. 13/780,402, now U.S. Pat. No. 9,795,379, issued Oct. 24, 2017, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. patent application Ser. No. 13/780,417, entitled "Installation Features for Surgical Instrument End Effector Cartridge," filed Feb. 28, 2013, now U.S. Pat. No. 9,808,248, issued Nov. 7, 2017, the disclosure of which is incorporated by reference herein. Anvil (18) may be constructed in accordance with at least some of the teachings of U.S. patent application Ser. No. 13/780,106, entitled "Integrated Tissue Positioning and Jaw Alignment Features for Surgical Stapler," filed Feb. 28, 2013, now U.S. Pat. No. 9,517,065, issued Dec. 13, 2016, the disclosure of which is incorporated by reference herein; at least some of the teachings of U.S. patent application Ser. No. 13/780,120, entitled "Jaw Closure Feature for End Effector of Surgical Instrument," filed Feb. 28, 2013, published as U.S. Pub. No. 2014/0239036 on Aug. 28, 2014, the disclosure of which is incorporated by reference herein; and/or at least some of the teachings of U.S. patent application Ser. No. 13/780,379, entitled "Staple Forming Features for Surgical Stapling Instrument," filed Feb. 28, 2013, published as U.S. Pub. No. 2014/0239037 on Aug. 28, 2014, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. patent application Ser. No. 13/780,082, entitled "Lockout Feature for Movable Cutting Member of Surgical Instrument," filed Feb. 28, 2013, now U.S. Pat. No. 9,717,497, issued Aug. 1, 2017, the disclosure of which is incorporated by reference herein. Other suitable forms that firing beam (14) may take will be apparent to those of ordinary skill in the art in view of the teachings herein.

Figure 3:
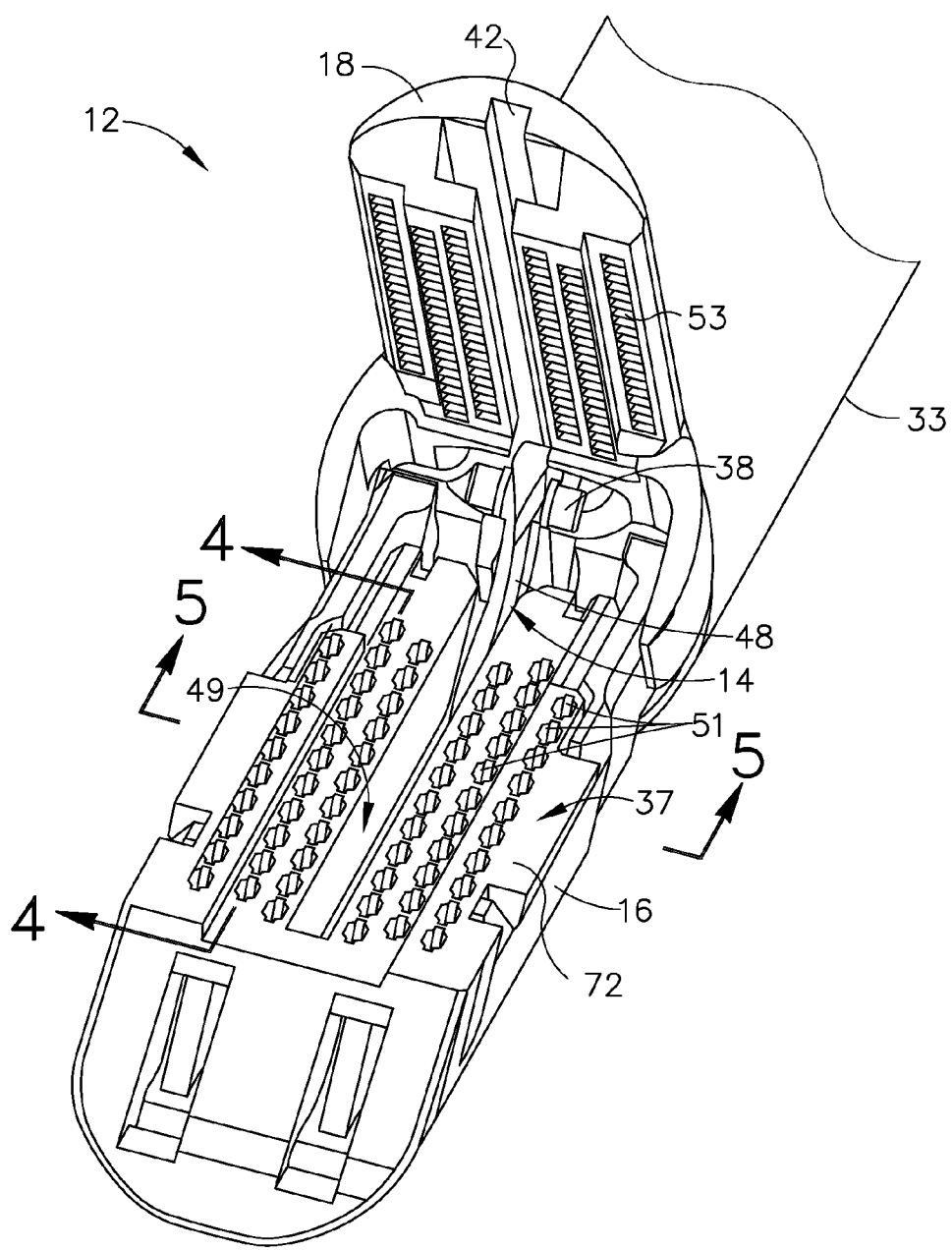
FIG. 3 depicts a perspective view of an opened end effector of the instrument of FIG. 1.
Figure 4A:
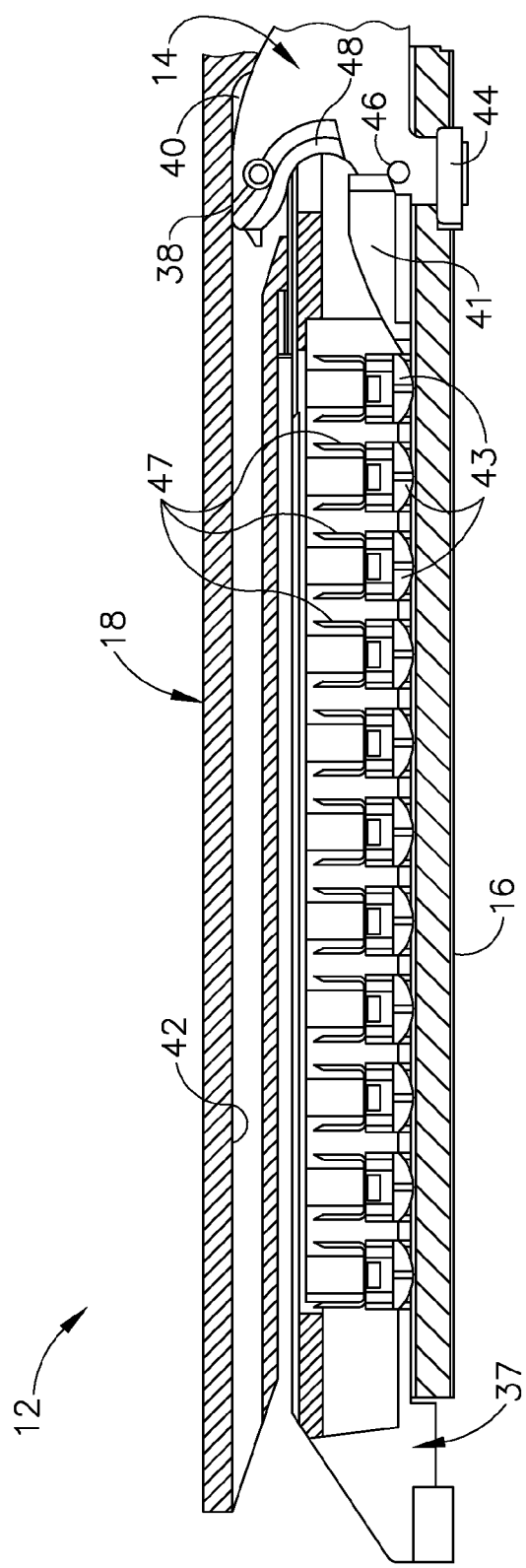
FIG. 4A depicts a side cross-sectional view of the end effector of FIG. 3, taken along line 4-4 of FIG. 3, with the firing beam in a proximal position.
Figure 4B:
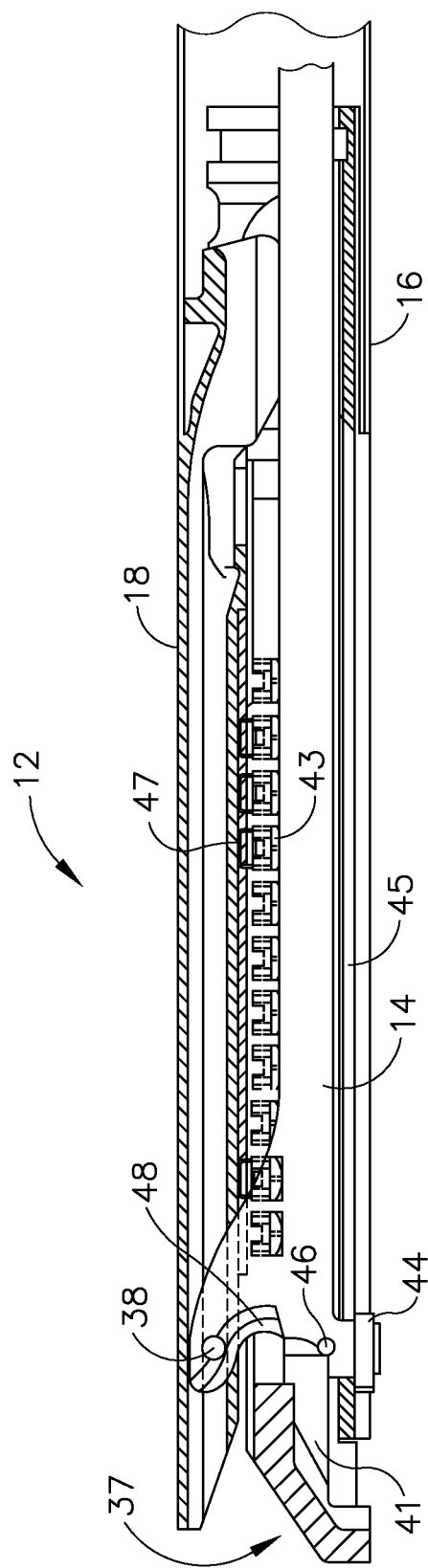
FIG. 4B depicts a side cross-sectional view of the end effector of FIG. 3, taken along line 4-4 of FIG. 3, with the firing beam in a distal position.
Figure 5:
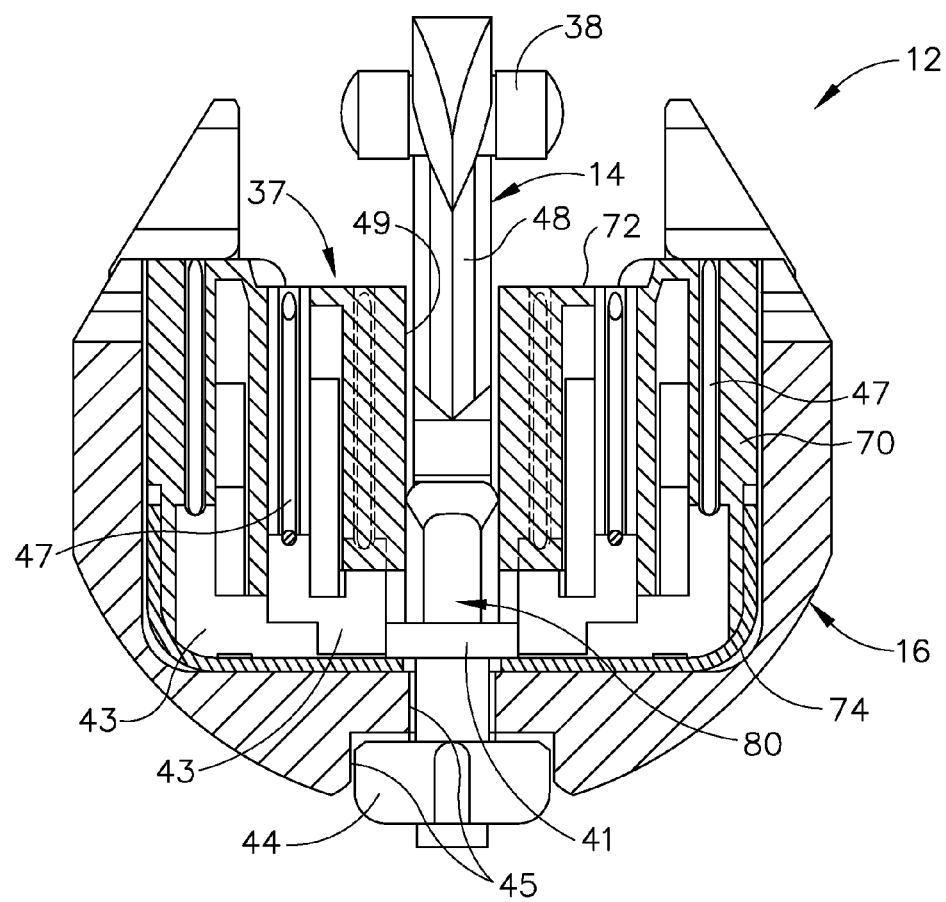
FIG. 5 depicts an end cross-sectional view of the end effector of FIG. 3, taken along line 5-5 of FIG. 3.
Figure 6:
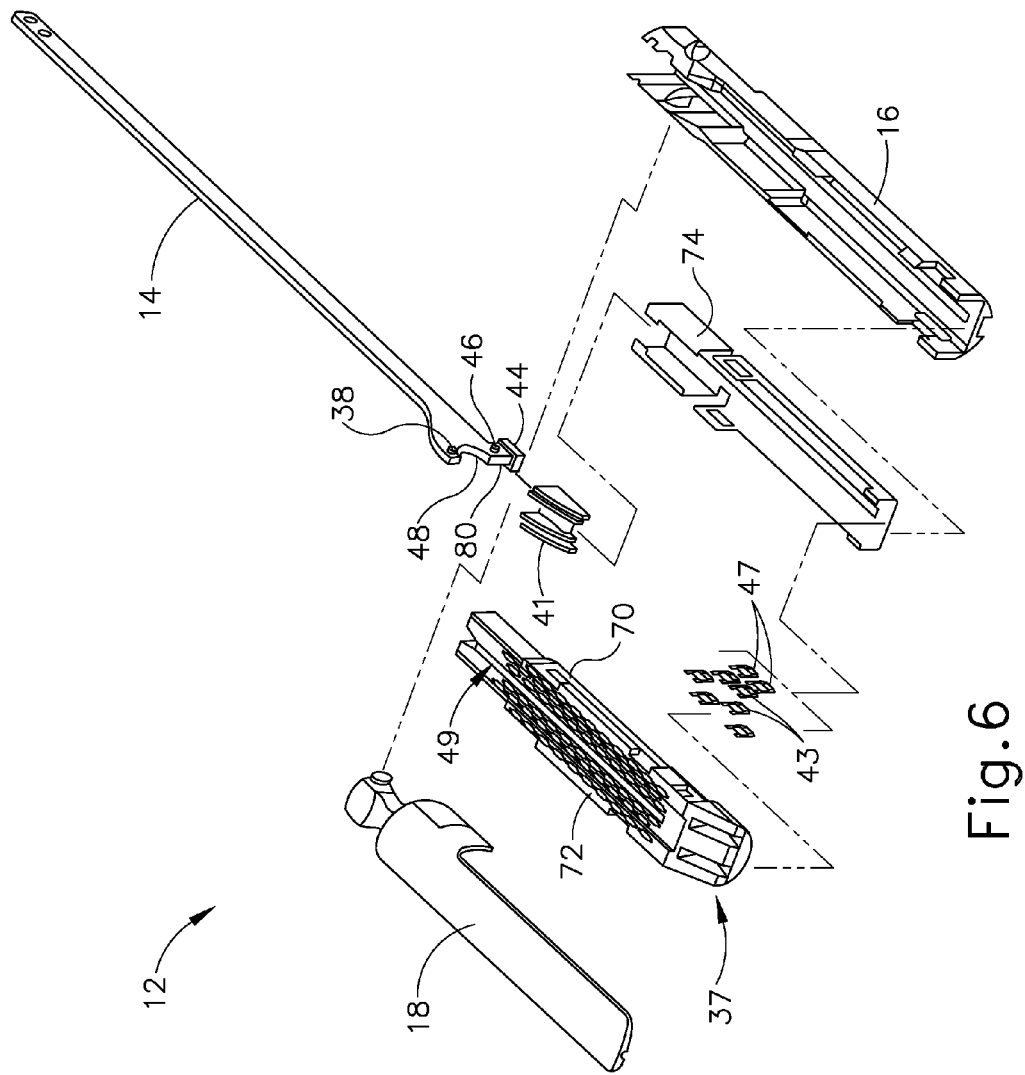
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106, now U.S. Pat. No. 9,517,065, issued Dec. 13, 2016, the disclosure of which is incorporated by reference herein. In addition or in the alternative, staple cartridge (37) may be constructed and operable in accordance with at least some of the teachings of U.S. patent application Ser. No. 13/780,417, now U.S. Pat. No. 9,808,248, issued Nov. 7, 2017, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
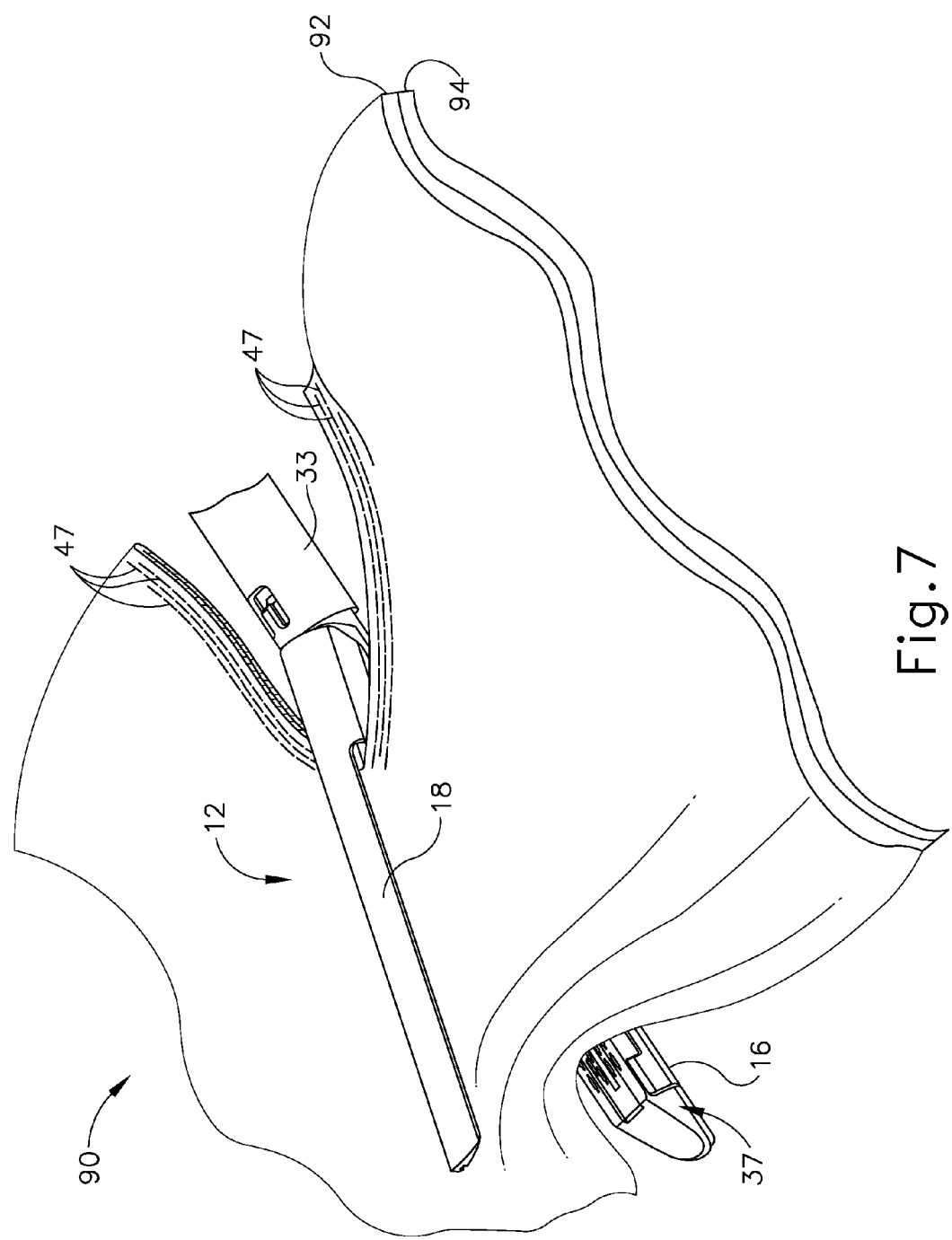
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; U.S. Pub. No. 2010/0264193, issued as U.S. Pat. No. 8,408,439; and/or 2012/0239012, issued as U.S. Pat. No. 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
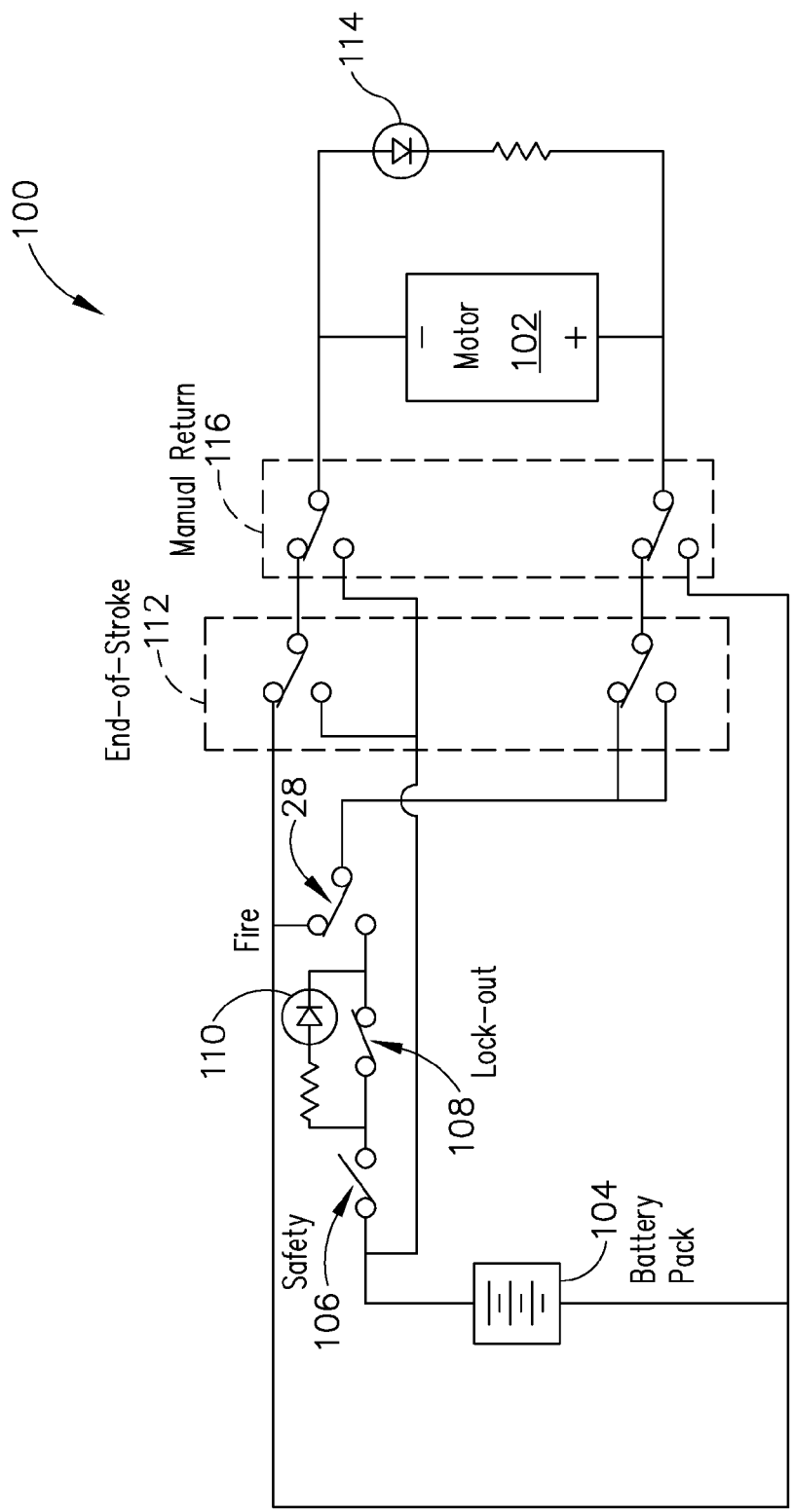
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
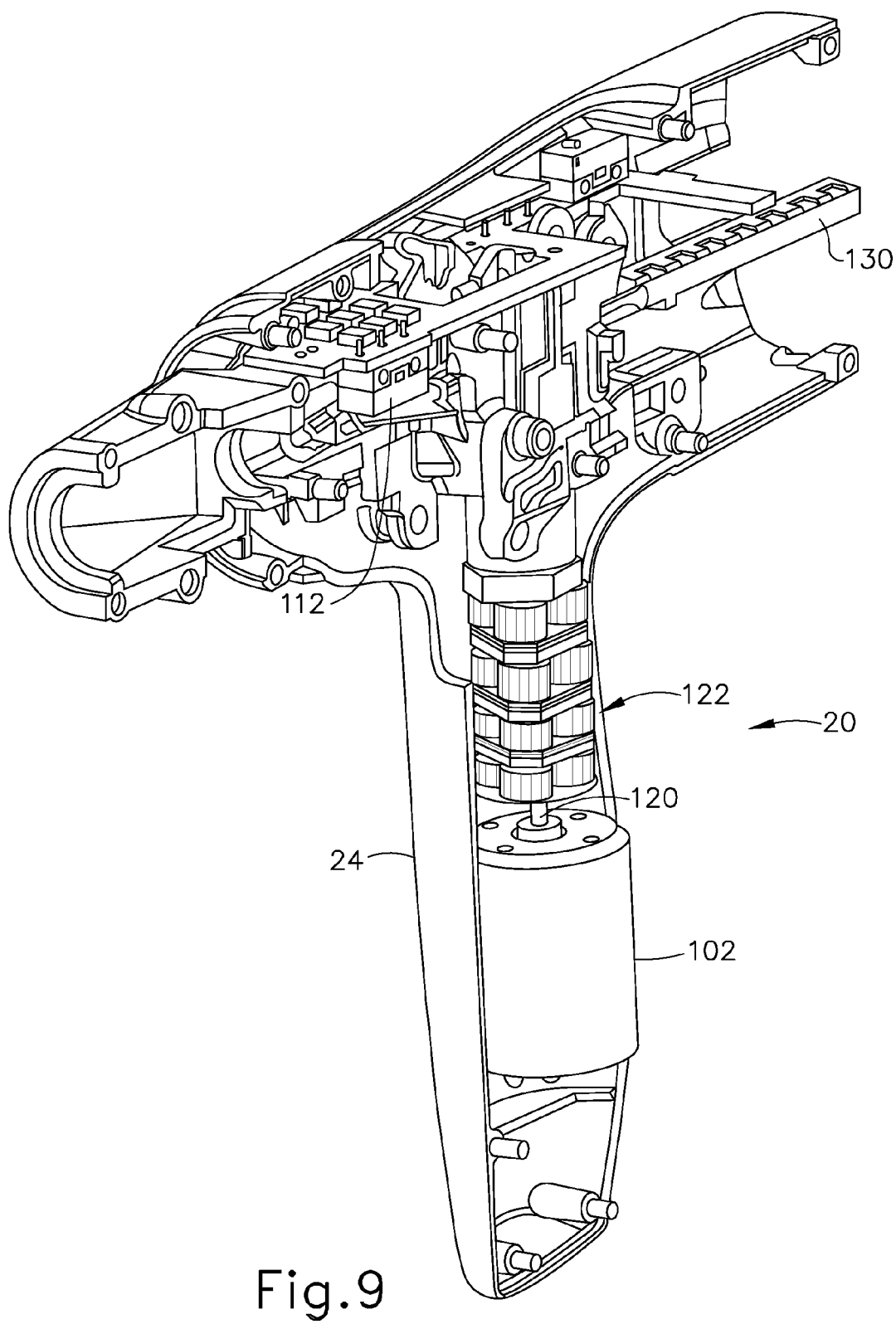
FIG. 9 depicts a perspective view of the handle assembly of the instrument of FIG. 1, with a housing half removed.
Figure 10:
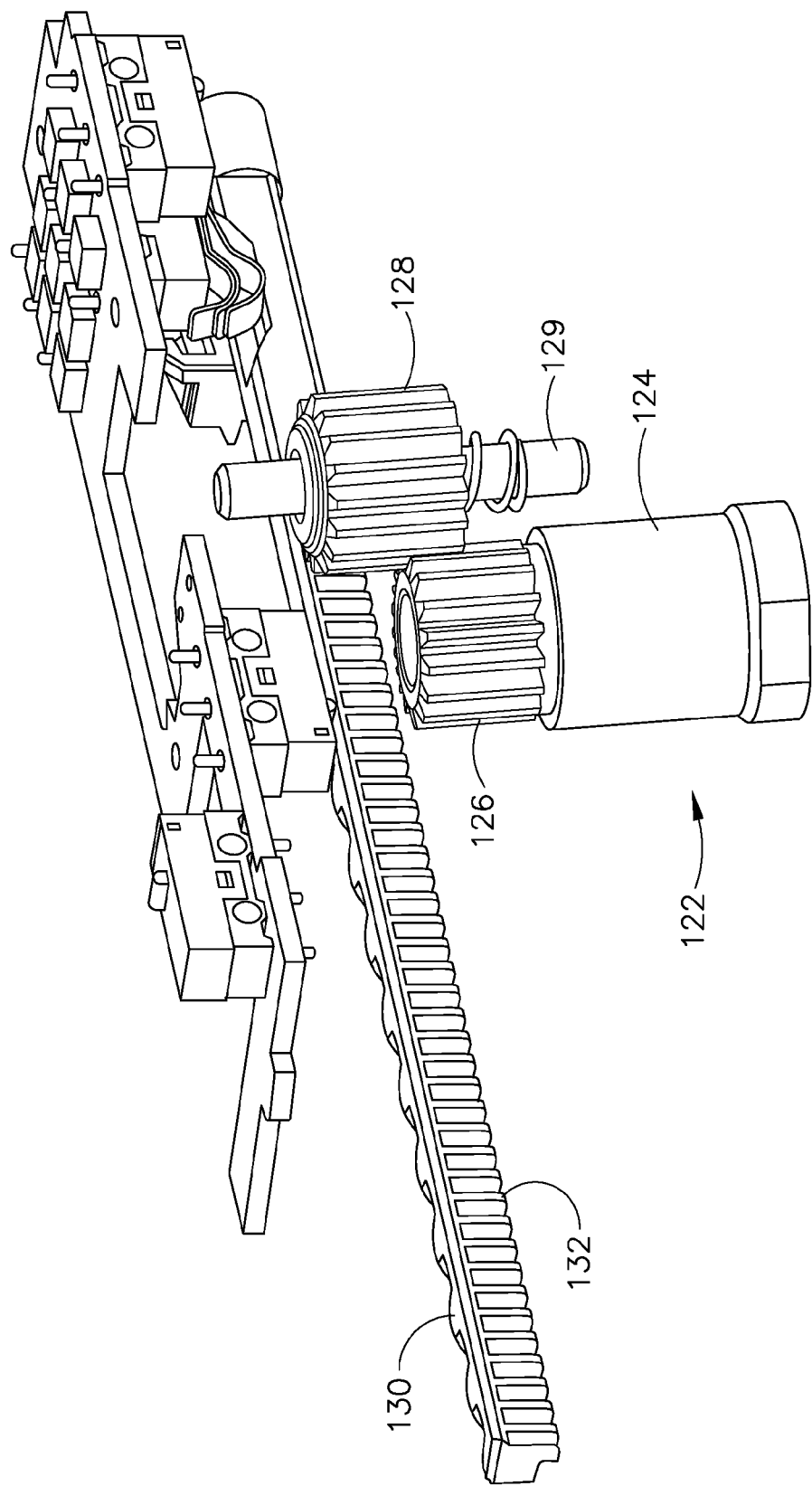
FIG. 10 depicts a perspective view of drive assembly components from the handle assembly of FIG. 9.
Figure 11:
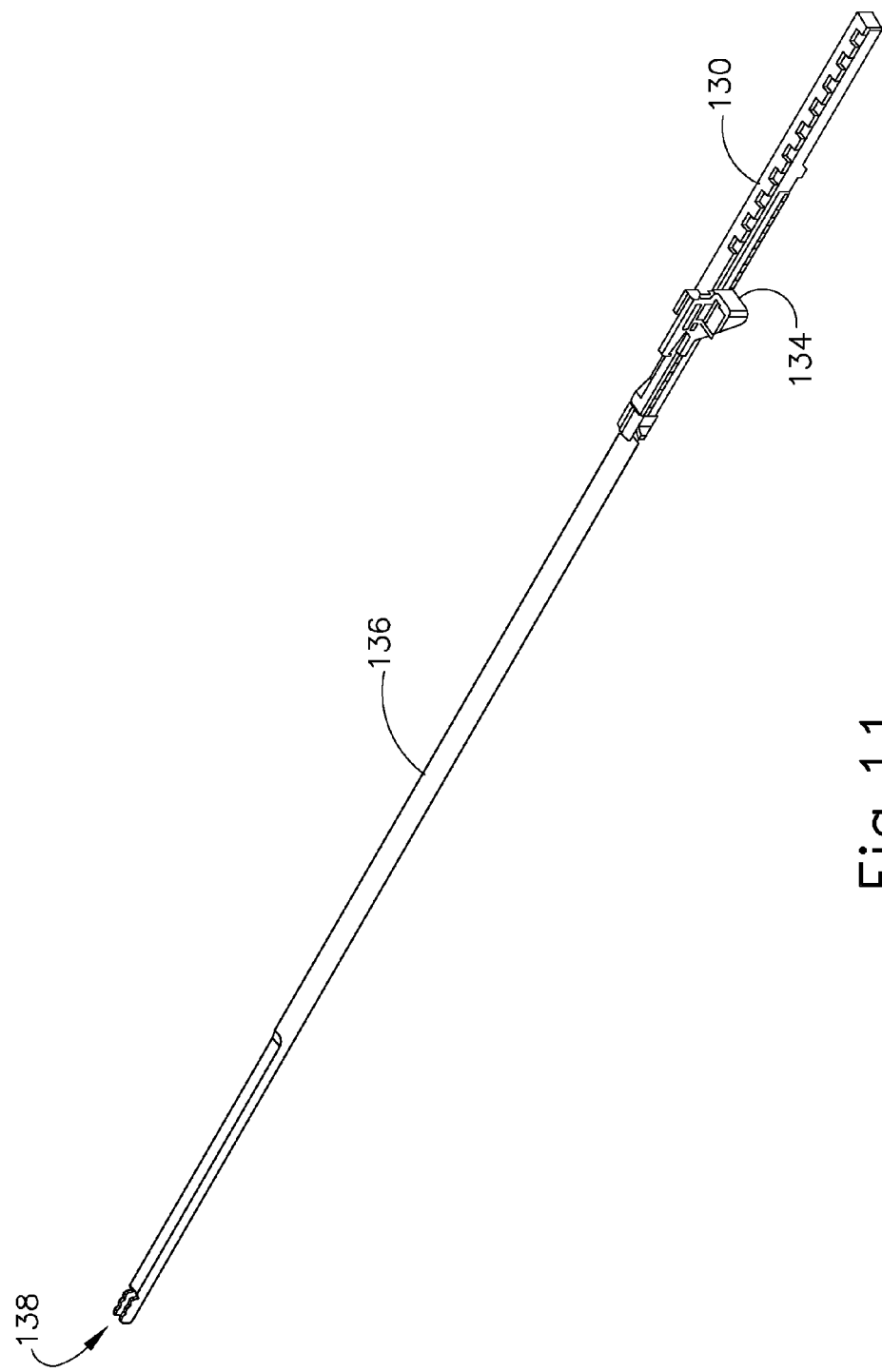
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012, issued as U.S. Pat. No. 8,453,914, the disclosure of which is incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary Articulation Joint Locking Features

In some instances, it may be desirable to lock articulation joint (11) to maintain end effector (12) at a desired articulation position. For example, articulation joint (11) may be locked after actuating articulation joint (11) to position end effector (12) at the desired angle (α). This may prevent inadvertent movement of end effector (12) after end effector (12) is positioned at the desired angle (α). Accordingly, articulation joint locking features may be provided to selectively unlock articulation joint (11) to permit adjustment of desired angle (α) and to selectively lock articulation joint (11) to maintain end effector (12) at desired angle (α). The examples below include several merely illustrative versions of articulation joint locking features that may be readily introduced to a surgical instrument (10).

Figure 12:
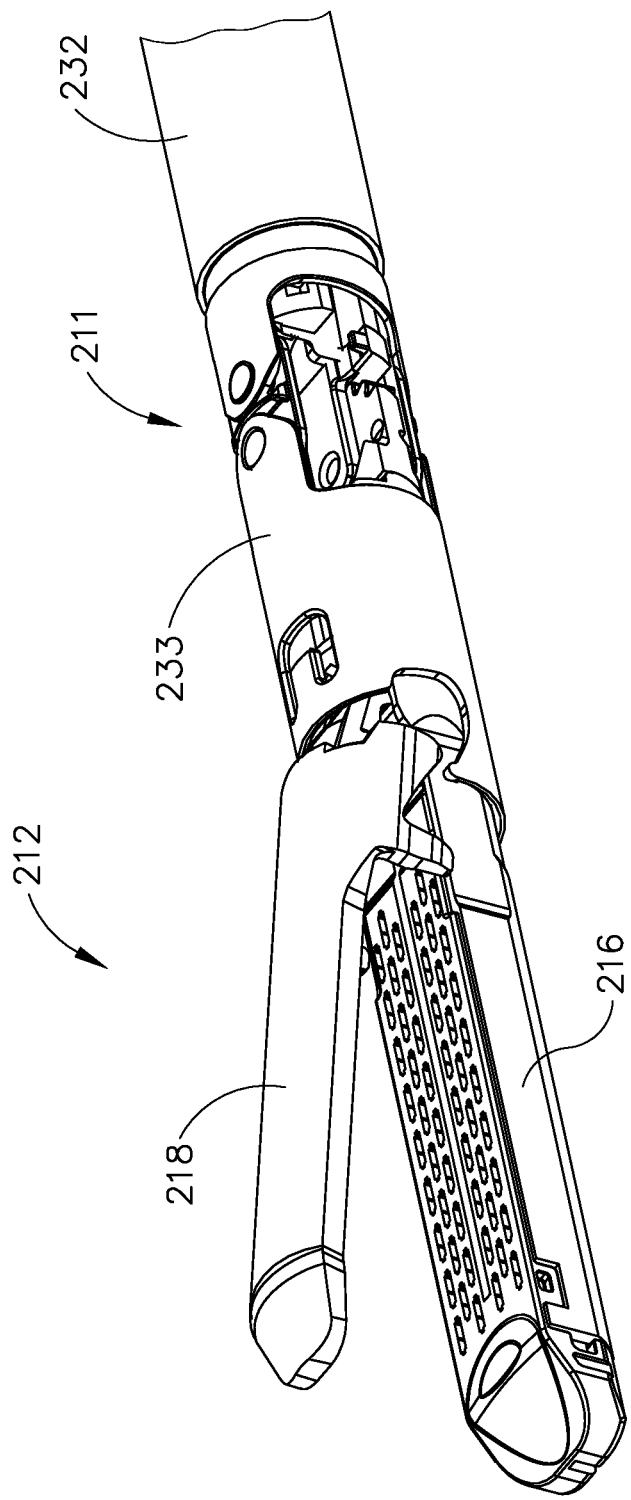
FIG. 12 depicts a perspective view of another exemplary end effector for use with the instrument of FIG. 1.
Figure 13:
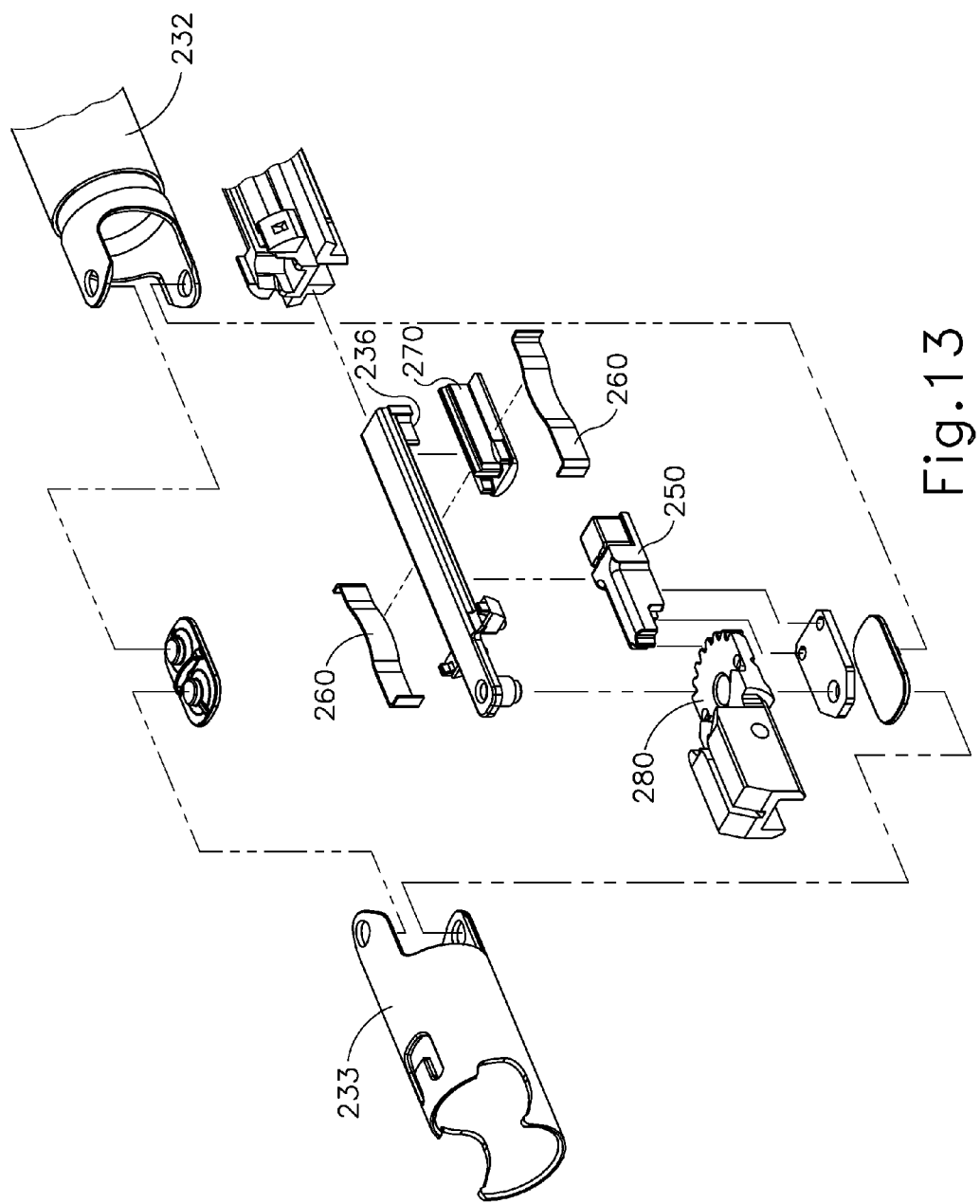
FIG. 13 depicts an exploded view of the articulation joint of FIG. 12.

FIGS. 12-13 show an exemplary end effector (212) and articulation joint (211) with articulation joint locking features that may be readily incorporated into instrument (10). End effector (212) comprises a lower jaw (216), a pivotable anvil (218), and a closure ring (233). End effector (212) is similar to end effector (12), except that the proximal end of lower jaw (216) comprises an articulation gear (280), as shown in FIG. 13. Articulation gear (280) comprises teeth (282) configured to couple with articulation joint (211). Articulation gear (280) is operable to rotate relative to articulation joint (211) such that end effector (212) is deflected from the longitudinal axis of shaft (22) to desired angle (α). Articulation joint (211) is similar to articulation joint (11), except that articulation joint (211) comprises a locking bar (250), a pair of springs (260), and a locking sled (270). FIG. 13 shows locking bar (250) positioned proximal of articulation gear (280). The pair of springs (260) are partially housed within locking bar (250) such that springs (260) extend proximally from locking bar (250). Locking sled (270) is positioned over the portion of springs (260) extending from locking bar (250).

Figure 14:
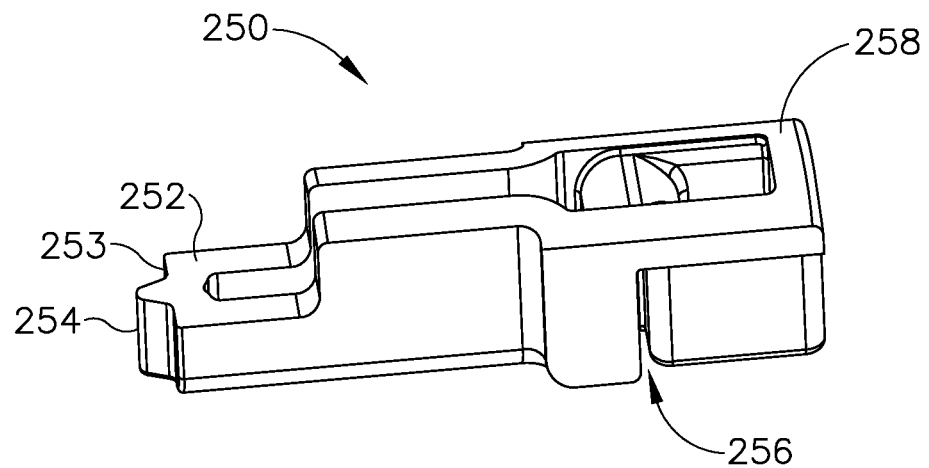
FIG. 14 depicts a perspective view of an exemplary locking bar of the articulation joint of FIG. 12.
Figure 15:
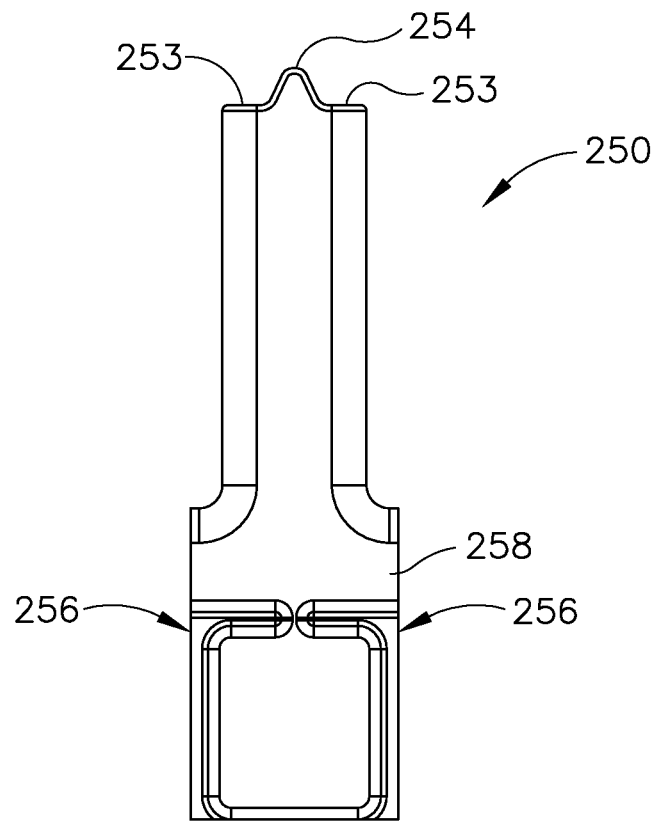
FIG. 15 depicts a bottom view of the locking bar of FIG. 14.

FIGS. 14-15 show locking bar (250) in greater detail. Locking bar (250) comprises a distal portion (252) with a wall (253) and a tip (254) extending distally from wall (253). Tip (254) is sized to correspond to teeth (282) of articulation gear (280) such that tip (254) fits between teeth (282). Proximal portion (258) of locking bar (250) comprises a pair of channels (256) to house springs (260). Channels (256) extend along each side of locking bar (250) and bend inwardly, as shown in FIG. 15. The inward bend of channels (256) are configured to maintain springs (260) within locking bar (250).

Figure 16:
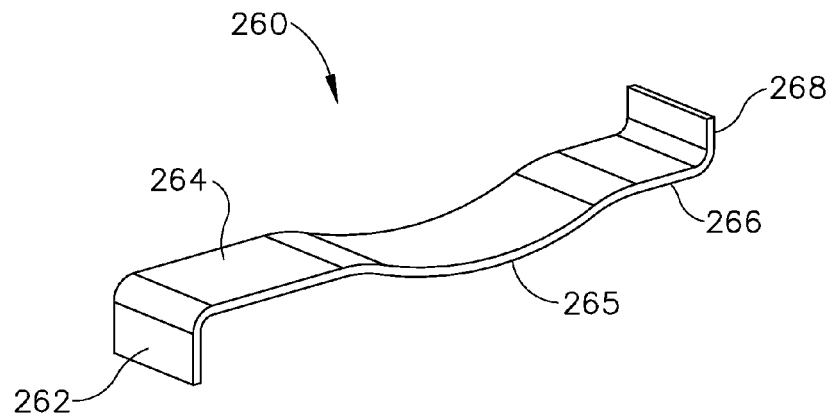
FIG. 16 depicts a perspective view of an exemplary spring of the articulation joint of FIG. 12.
Figure 17:
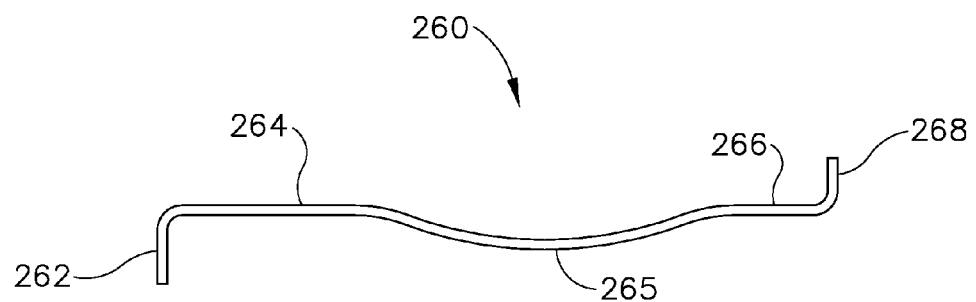
FIG. 17 depicts a top view of the spring of FIG. 16.

Each spring (260) comprises a distal end (262), a distal portion (264), an arcuate portion (265), a proximal portion (266), and a proximal end (268). As shown in FIGS. 16-17, distal portion (264) is substantially flat and is configured to partially reside within the side portions of channels (256). Distal end (262) extends inwardly from distal portion (264) to correspond to channel (256). Arcuate portion (265) is proximal to distal portion (264) and bends inwardly in a circular configuration. Proximal portion (266) is adjacent to arcuate portion (265) and is substantially flat. Proximal end (268) extends outwardly from proximal portion (266). Proximal end (268) is configured to engage with a wall (236) of articulation joint housing (232) such that housing (232) maintains the lateral position of proximal end (268). Housing (232), locking bar (250), wall (236), and channel (256) cooperate to house two springs (260) facing in opposite directions such that each distal end (262) extends inwardly within articulation joint (211) and each proximal end (268) extends outwardly within articulation joint (211). Although two springs (260) are shown, any other number of springs (260) may be used. Because each distal end (262) is maintained within locking bar (250) and each proximal end (268) is maintained within housing (232), each spring (260) is operable to compress as locking bar (250) translates proximally such that each arcuate portion (265) of springs (260) buckles by flexing inwardly.

FIGS. 18-20 show locking sled (270), which comprises a body (272), a central protrusion (276), and side protrusions (274). Body (272) comprises a recess (271) extending transversely across body (272), as shown in FIG. 18. Recess (271) may engage a feature of closure tube (32) proximal to articulation joint (211) such that when the feature of closure tube (32) is translated distally and/or proximally by closure trigger (26), locking sled (270) is also translated distally and/or proximally. Accordingly, if closure trigger (26) is actuated toward pistol grip (24) to close end effector (212), closure tube (32) may translate distally to translate locking sled (270). If closure trigger (26) is released from pistol grip (24) to open end effector (212), closure tube (32) may translate proximally to translate locking sled (270) proximally. Other suitable methods to translate locking sled (270) will be apparent to one with ordinary skill in the art in view of the teachings herein. Central protrusion (276) of locking sled (270) extends downward from substantially the center of body (272). As shown in FIG. 20, central protrusion (276) comprises a distal wall (277) and two side walls (279). Wall (277) extends transversely across body (272) and side walls (279) extend along the length of body (272). Wall (277) and side walls (279) are joined by chamfered lead-in surfaces (278). Central protrusion (276) is configured to translate between the pair of springs (260). Side protrusions (274) of locking sled (270) extend downwardly from each side of the distal portion of body (272). As shown in FIG. 20, each side protrusion (274) comprises a distal camming surface (273) and a proximal camming surface (275). Camming surfaces (273, 275) are configured to engage arcuate portions (265) of springs (260).

Figure 21A:
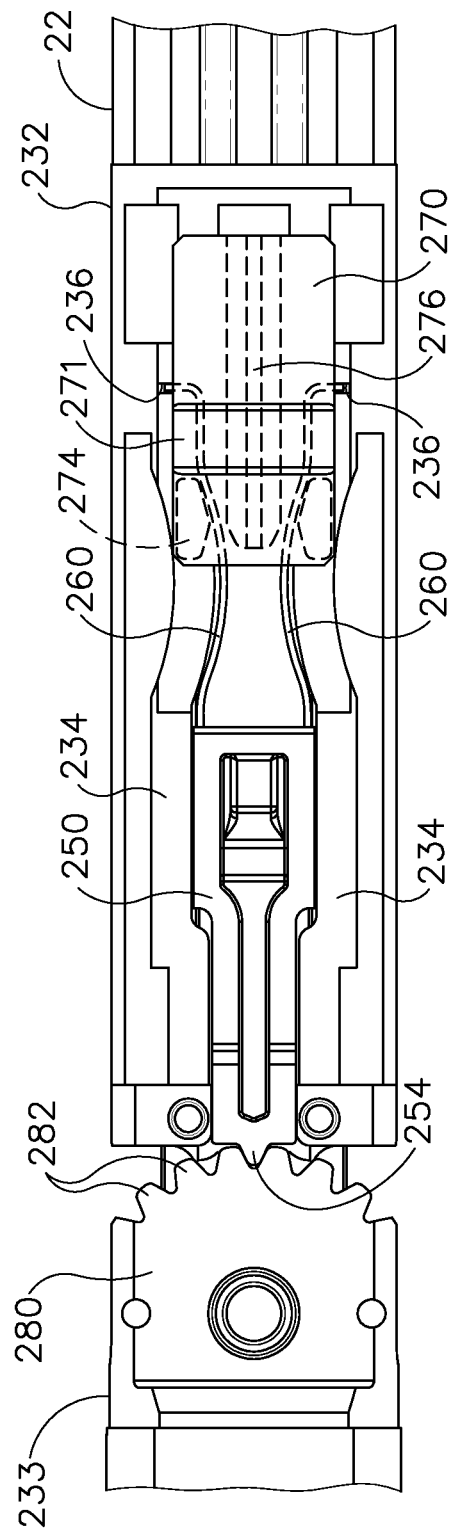
FIG. 21A depicts a partial view of the articulation joint of FIG. 12 in a non-articulated and unlocked position, with an outer sheath omitted.
Figure 22A:
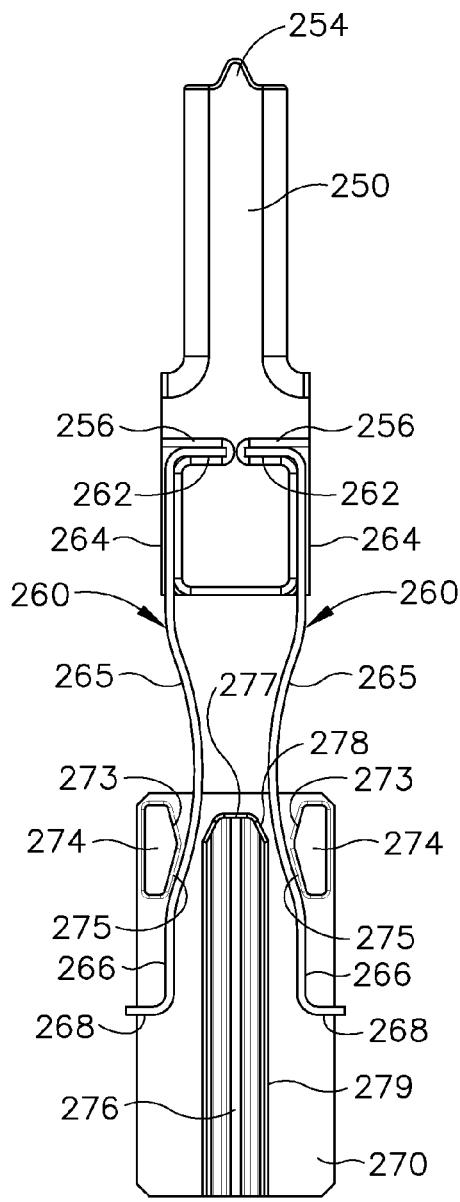
FIG. 22A depicts a bottom view of the locking bar, springs, and locking sled of the articulation joint of FIG. 12 in the unlocked position.

In an exemplary use, instrument (10) may be inserted to a surgical site in a nonarticulated state, with jaws (216, 218) closed. When jaws (216, 218) are in the closed position, articulation joint (211) is locked, as described in more detail below. Once end effector (212) and articulation joint (211) are inserted within the patient, jaws (216, 218) may be opened, thereby unlocking articulation joint (211) and allowing end effector (212) to be positioned at the desired angle (α). FIG. 21A shows articulation joint (211) in the nonarticulated and unlocked position. Locking bar (250) is in a distal position such that tip (254) is positioned between teeth (282) of articulation gear (280). Springs (260) extend proximally from locking bar (250) and are housed within channels (256) of locking bar (250), as shown in FIG. 22A. Because locking bar (250) is in the distal position, springs (260) are in a nominal position. Proximal end (268) of springs (260) couple with wall (236) of housing (232) to maintain the lateral and proximal position of springs (260). Springs (260) resiliently bias locking bar (250) to the distal position to engage tip (254) with teeth (282) of articulation gear (280). Locking sled (270) is positioned over springs (260) in a proximal and unlocked position. In the unlocked position, shown in FIG. 22A, proximal camming surfaces (275) engage a proximal portion of arcuate portions (265) of springs (260). Central protrusion (276) of locking sled (270) is positioned between springs (260), but is disengaged from springs (260). Because central protrusion (276) is not in contact with springs (260) and does not otherwise impede buckling of springs (260), springs (260) are free to buckle inwardly to enable proximal movement of locking bar (250) to thereby allow the articulation of joint (211).

Figure 21B:
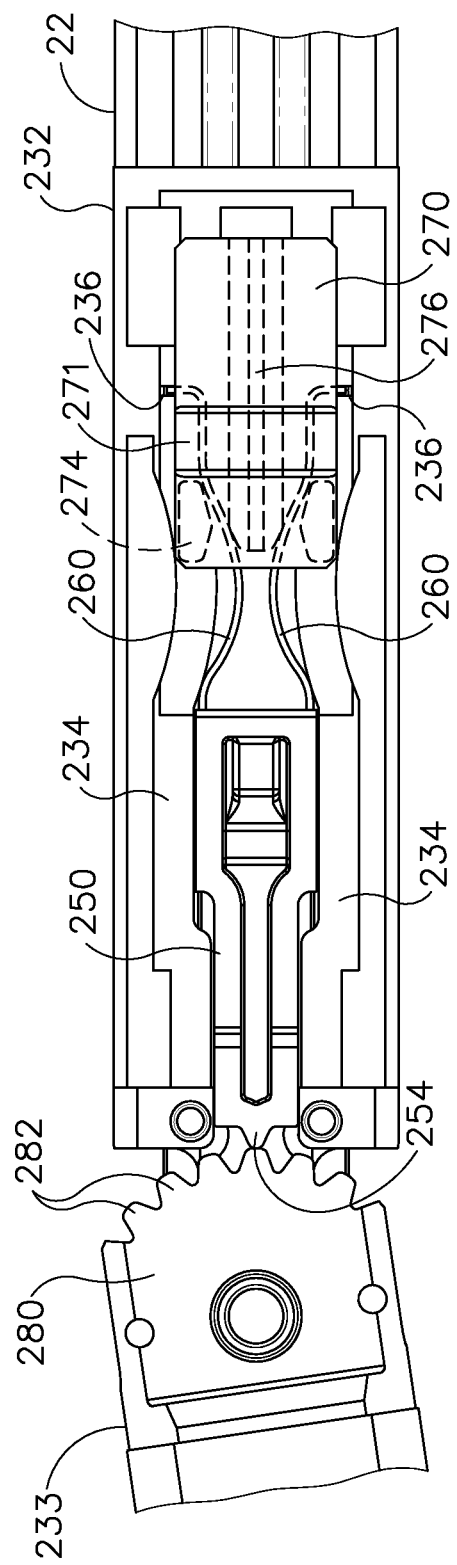
FIG. 21B depicts a partial view of the articulation joint of FIG. 12 being articulated in the unlocked position, with the outer sheath omitted.

Once articulation joint (211) and end effector (212) are inserted to the desired surgical site within the patient and articulation joint (211) is unlocked, articulation joint (211) may be remotely articulated by an articulation control (13), such that end effector (212) may be deflected to a desired angle (α). Alternatively, articulation joint (211) may be articulated by pressing the distal end of end effector (212) against an anatomical structure in the patient to pivot end effector (212) at articulation joint (211). Another instrument (e.g., graspers) may also be used to pivot end effector (212) at articulation joint (211). Suitable methods for articulating end effector (212) at articulation joint (211) will be apparent to one with ordinary skill in the art in view of the teachings herein. As shown in FIG. 21B, when articulation control (13) is actuated or when end effector (212) is otherwise articulated, closure ring (233) and articulation gear (280) of lower jaw (216) are rotated relative to shaft (22) at articulation joint (211). As articulation gear (280) is rotated, tip (254) of locking bar (250) is ratcheted along teeth (282) of articulation gear (280) such that tip (254) slides from between teeth (282) to the tip of teeth (282). This pushes locking bar (250) to a proximal position. When locking bar (250) translates to the proximal position, locking bar (250) compresses springs (260). When springs (260) compress, distal ends (262) of springs (260) translate with locking bar (250). Proximal ends (268) are fixed to wall (236) of housing (232) to maintain the lateral and proximal position of proximal ends (268). This causes arcuate portions (265) of springs (260) to flex inwardly. Because locking sled (270) is in the proximal and unlocked position, locking sled (270) allows springs (260) to flex inwardly. The compression of springs (260) exert a force on locking bar (250) in the distal direction such that tip (254) of locking bar (250) is continuously engaged with articulation gear (280).

Figure 21C:
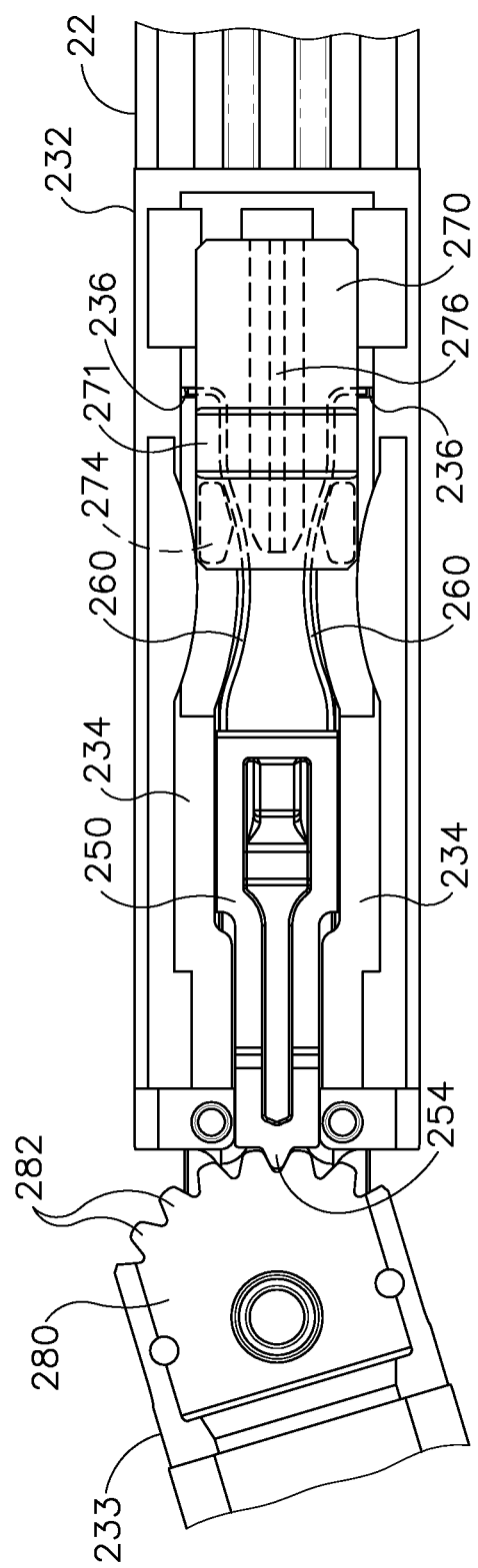
FIG. 21C depicts a partial view of the articulation joint of FIG. 12 in an articulated and unlocked position, with the outer sheath omitted.

As articulation gear (280) continues to rotate, springs (260) push locking bar (250) distally to once again engage articulation gear (280) between teeth (282), as shown in FIG. 21C. Locking bar (250) remains in contact with articulation gear (280) throughout the articulation. Springs (260) return to the nominal position. Locking sled (270) remains in the proximal and unlocked position. Once end effector (212) is articulated to a desired angle ($\alpha$), closure trigger (26) may then be actuated toward pistol grip (24) to cause the closing of anvil (218) toward lower jaw (216). Such closing of anvil is provided through a closure tube (32) and closure ring (233), which both longitudinally translate relative to handle portion (20) in response to pivoting of closure trigger (26) relative to pistol grip (24). Articulation joint (211) is operable to communicate longitudinal movement from closure tube (32) to closure ring (233).

Figure 21D:
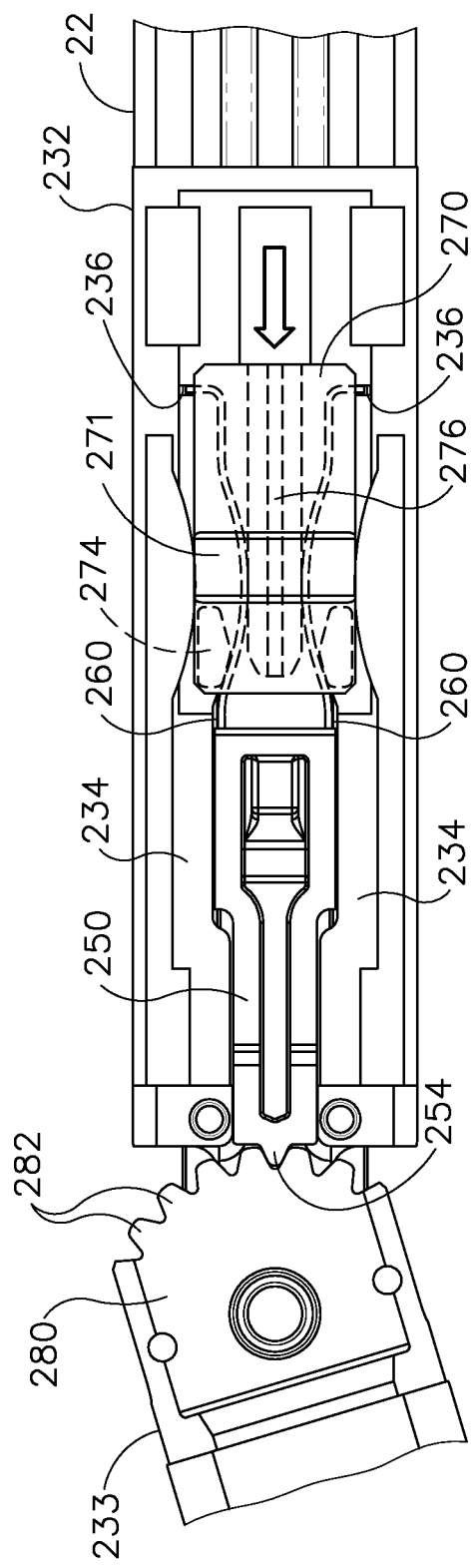
FIG. 21D depicts a partial view of the articulation joint of FIG. 12 in an articulated and locked position, with the outer sheath omitted.
Figure 22B:
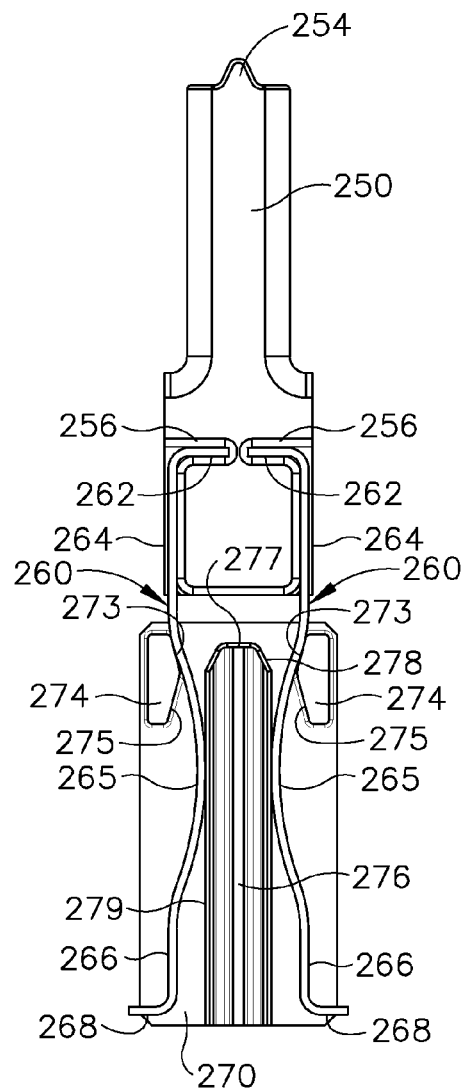
FIG. 22B depicts a bottom view of the locking bar, springs, and locking sled of the articulation joint of FIG. 12 in the locked position.

When closure tube (32) is translated distally to close end effector (212), closure tube (32) also translates locking sled (270) distally. When locking sled (270) is translated to a distal position, locking sled (270) locks articulation joint (211), as shown in FIG. 21D. When articulation joint (211) is in the locked position, locking bar (250) is engaged between teeth (282) of articulation gear (280). Springs (260) are in the nominal position. Locking sled (270) is in the distal position to engage springs (260). As shown in FIG. 22B, distal camming surfaces (273) of side protrusions (274) engage a distal portion of arcuate portions (265) of springs (260). Central protrusion (276) is translated between springs (260) and engages the inner surfaces of arcuate portions (265). Chamfered lead-in surfaces (278) of central protrusion (276) allow central protrusion (276) to translate smoothly within springs (260). Protrusions (274, 276) of locking sled (270) engage springs (260) to prevent springs (260) from compressing and flexing inwardly. This prevents locking bar (250) from translating proximally, which maintains tip (254) of locking bar (250) between teeth (282) of articulation gear (280) to prevent articulation gear (280) from rotating. Accordingly, locking sled (270) prevents articulation of end effector (212) when jaws (216, 218) of end effector (212) are closed to prevent inadvertent movement of end effector (212) during stapling. Alternatively, the translation of locking sled (270) may be decoupled from closure trigger (26) such that locking sled (270) may be translated independently of jaws (216, 218) to selectively lock and/or unlock articulation joint (211).

Once end effector (212) is closed, the tissue captured between anvil (218) and lower jaw (216) may be cut and stapled. To open end effector (212), closure trigger (26) may be released away from pistol grip (24) to translate closure tube (32) and closure ring (233) proximally and pivot anvil (218). When closure trigger (26) is released, closure tube (32) may be coupled to locking sled (270) to translate locking sled (270) proximally. This may return locking sled (270) to the position shown in FIG. 21C to unlock articulation joint (211). Alternatively, the translation of locking sled (270) may be decoupled from closure trigger (26) such that locking sled (270) may be translated independently of jaws (216, 218) to selectively lock and/or unlock articulation joint (211). End effector (212) may then be returned to the nonarticulated position, shown in FIG. 21A. Accordingly, jaws (216, 218) may be closed to re-lock articulation joint (211) and instrument (10) may then be removed from the surgical site. Staple cartridge (37) may be replaced with a new staple cartridge, and end effector (212) may be again inserted to the surgical site for further cutting and stapling.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued Dec. 31, 2013 as U.S. Pat. No. 8,616,431, the disclosure of which is incorporated by reference herein; U.S. Pub. No. 2012/0199633, entitled "Surgical Stapling Instruments with Cam-Driven Staple Deployment Arrangements," published Aug. 9, 2012, issued Nov. 5, 2013 as U.S. Pat. No. 8,573,461, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued Dec. 10, 2013 as U.S. Pat. No. 8,602,288, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued Jul. 9, 2013 as U.S. Pat. No. 8,479,969; U.S. Pub. No. 2012/0138660, entitled "Robotically-Controlled Cable-Based Surgical End Effectors," published Jun. 7, 2012, now U.S. Pat. No. 8,800,838, issued Aug. 12, 2014, the disclosure of which is incorporated by reference herein; and/or U.S. Pub. No. 2012/0211546, entitled "Robotically-Controlled Surgical End Effector System with Rotary Actuated Closure Systems," published Aug. 16, 2012, issued Nov. 5, 2013 as U.S. Pat. No. 8,573,465, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a shaft having a longitudinal axis;
   (b) an end effector, wherein the end effector is pivotable from a first position to a second position, wherein the end effector is aligned with the longitudinal axis of the shaft in the first position, wherein the end effector is angled relative to the longitudinal axis of the shaft in the second position;
   (c) an articulation joint coupling the shaft with the end effector, wherein the articulation joint is operable to pivot the end effector from the first position to the second position; and
   (d) a locking feature coupled with the articulation joint, wherein the locking feature is movable from a proximal position to a distal position, wherein the locking feature is operable to lock the articulation joint in the distal position, wherein the locking feature includes:
      (i) a first locking member selectively movable between an unlock position and a lock position, and
      (ii) a second locking member movable between the proximal position and the distal position and operatively connected to the first locking member, wherein the second locking member is biased toward the distal position against the end effector, wherein the second locking member with the first locking member in the lock position inhibits proximal movement of the second locking member to thereby lock pivoting of the end effector,
      (iii) at least one resilient member configured to flex inwardly toward a longitudinal axis of the locking feature when the first locking member is in the unlock position and the second locking member moves proximally,
   wherein the first locking member is selectively movable between the unlock and lock positions selectively moves relative to the second locking member while the second locking member remains stationary.

2. The apparatus of claim 1, wherein the first locking member comprises a locking sled that is translatable between the unlock position and the lock position.

3. The apparatus of claim 2, wherein the locking sled comprises a first protrusion extending downwardly from a central portion of a body of the locking sled.

4. The apparatus of claim 3, wherein the locking sled comprises a second protrusion extending downwardly from a side portion of the body of the locking sled.

5. The apparatus of claim 2, wherein the at least one resilient member biases the second locking member toward the distal position against the end effector, wherein the locking sled in the lock position engages the at least one resilient member to prevent the at least one resilient member from flexing and thereby inhibit proximal movement of the second locking member.

6. The apparatus of claim 5, wherein the second locking member comprises a locking bar, wherein the locking bar is coupled with the at least one resilient member.

7. The apparatus of claim 6, wherein the locking bar comprises at least one channel, wherein the channel is configured to house at least a portion of the at least one resilient member.

8. The apparatus of claim 6, wherein the locking bar is translatable from the distal position to the proximal position, wherein the locking bar is operable to compress the at least one resilient member in the proximal position, and wherein the at least one resilient member is configured to bias the locking bar distally.

9. The apparatus of claim 8, wherein the locking bar comprises a distal tip, and wherein the distal tip is biased against the end effector.

10. The apparatus of claim 9, wherein a proximal portion of the end effector comprises a gear, wherein the distal tip of the locking bar is configured to engage the gear of the end effector.

11. The apparatus of claim 10, wherein the locking sled is operable to lock the gear of the end effector when the locking sled is in the lock position.

12. The apparatus of claim 5, wherein the at least one resilient member is configured to flex inwardly as the second locking member translates proximally.

13. The apparatus of claim 1, wherein the end effector comprises a first jaw and a second jaw, wherein the first jaw is pivotable relative to the second jaw.

14. The apparatus of claim 13, comprising an actuator, wherein the actuator is operable to simultaneously pivot the first jaw and move the first locking member.

15. The apparatus of claim 14, wherein the first locking member is fixedly secured to the actuator.

16. The apparatus of claim 13, wherein the second jaw comprises a gear on a proximal portion of the second jaw, wherein the gear is couplable with the locking feature.

17. An apparatus comprising:
(a) an end effector, wherein the end effector is pivotable from a first position to a second position;
(b) an articulation joint coupled with the end effector, wherein the articulation joint is operable to pivot the end effector from the first position to the second position; and
(c) a locking feature coupled with the articulation joint, the locking feature comprising:
(i) a locking member that is movable between a proximal position and a distal position, wherein the locking member when in the distal position is configured to lock the articulation joint,
(ii) a locking sled that is movable between a lock position and an unlock position, and
(iii) at least one resilient member coupled with the locking sled and the locking member, wherein the locking sled is movable relative to the at least one resilient member, and wherein the locking sled when in the lock position is configured to engage the resilient member to prevent the resilient member from flexing and thereby prevent the locking member from moving proximally, Wherein the at least one resilient member is configured to flex inwardly toward the longitudinal axis of the locking feature when the locking sled is in the unlock position and the locking member moves proximally.

18. The apparatus of claim 12, wherein the locking sled in the lock position is positioned laterally against the at least one resilient member to prevent the at least one resilient member from flexing inwardly.

19. An apparatus comprising:
(a) a shaft having a longitudinal axis;
(b) an end effector, wherein the end effector is pivotable from a first position to a second position relative to the longitudinal axis of the shaft, wherein the end effector is angled relative to the longitudinal axis in at least one of the first position or the second position;
(c) an articulation joint coupling the shaft with the end effector, wherein the articulation joint is operable to pivot the end effector from the first position to the second position; and
(d) a locking feature coupled with the articulation joint, wherein the locking feature is movable from a proximal position to a distal position, wherein the locking feature is operable to lock the articulation joint in the distal position, wherein the locking feature includes:
(i) a first locking member selectively movable between an unlock position and a lock position, and
(ii) a second locking member movable between the proximal position and the distal position and operatively connected to the first locking member, wherein the second locking member is biased toward the distal position against a proximal portion of the end effector, wherein the second locking member with the first locking member in the unlock position is configured to contact the proximal portion of the end effector and detent movement of the end effector such that selective pivoting of the end effector between the first and second positions drives the second locking member proximally, and wherein the second locking member with the first locking member in the lock position inhibits proximal movement of the second locking member to thereby lock pivoting of the end effector, and
(iii) a resilient member configured to flex inwardly toward a longitudinal axis of the locking feature when the first locking member is in the unlock position and the second locking member moves proximally, wherein the second locking member remains in contact with the proximal portion of the end effector throughout pivoting movement thereof.

* * * * *